United States Patent [19]

Ensminger et al.

[11] Patent Number: 5,057,084
[45] Date of Patent: Oct. 15, 1991

[54] IMPLANTABLE INFUSION DEVICE
[75] Inventors: William D. Ensminger; James A. Knol; James C. Andrews, all of Ann Arbor, Mich.
[73] Assignee: The Regents of the University of Michigan, Ann Arbor, Mich.
[21] Appl. No.: 487,541
[22] Filed: Mar. 1, 1990
[51] Int. Cl.⁵ .................................... A61M 5/178
[52] U.S. Cl. ............................ 604/167; 604/175; 604/256
[58] Field of Search ............... 604/175, 167, 256, 93, 604/86, 244, 905, 283, 4, 8-10, 49; 128/DIG. 26
[56] References Cited

U.S. PATENT DOCUMENTS

| | | |
|---|---|---|
| 3,288,137 | 1/1964 | Lund . |
| 3,402,710 | 9/1968 | Paleschuck . |
| 3,565,078 | 2/1971 | Vaillancourt et al. . |
| 3,699,956 | 10/1972 | Kitrilakis et al. . |
| 4,181,132 | 1/1980 | Parks . |
| 4,190,040 | 2/1980 | Schulte . |
| 4,230,109 | 10/1980 | Geiss . |
| 4,256,102 | 3/1981 | Monaco . |
| 4,387,879 | 6/1983 | Tauschinski . |
| 4,405,320 | 9/1983 | Cracauer et al. . |
| 4,425,119 | 1/1984 | Berglund . |
| 4,430,081 | 2/1984 | Timmermans . |
| 4,439,188 | 3/1984 | Dennehey et al. . |
| 4,447,237 | 5/1984 | Frisch et al. . |
| 4,464,178 | 10/1984 | Dalton . |
| 4,490,137 | 12/1984 | Moukheibir . |
| 4,491,126 | 1/1985 | Cullor . |
| 4,543,088 | 9/1985 | Bootman et al. . |
| 4,547,194 | 10/1985 | Moorehead . |
| 4,569,675 | 2/1986 | Prosl et al. . |
| 4,578,061 | 3/1986 | Lemelson . |
| 4,578,063 | 3/1986 | Inmann et al. . |
| 4,581,020 | 4/1986 | Mittleman . |
| 4,623,329 | 11/1986 | Drobish et al. . |
| 4,634,422 | 1/1987 | Kantrowitz et al. . |
| 4,645,495 | 2/1987 | Vaillancourt . |
| 4,650,473 | 3/1987 | Bartholomew et al. . |
| 4,673,394 | 6/1987 | Fenton, Jr. et al. . |
| 4,682,981 | 7/1987 | Suzuki et al. . |
| 4,692,146 | 9/1987 | Hilger . |
| 4,695,273 | 9/1987 | Brown . |
| 4,704,103 | 11/1987 | Stober et al. . |
| 4,710,167 | 12/1987 | Lazorthes . |
| 4,710,174 | 12/1987 | Moden et al. . |
| 4,712,583 | 12/1987 | Pelmulder et al. . |
| 4,781,680 | 11/1988 | Redmond et al. . |
| 4,781,693 | 11/1988 | Martinez et al. . |
| 4,781,695 | 11/1988 | Dalton . |
| 4,790,826 | 12/1988 | Elftman . |
| 4,810,241 | 3/1989 | Rogers . |
| 4,842,591 | 6/1989 | Luther . |
| 4,857,053 | 8/1989 | Dalton . |
| 4,857,062 | 8/1989 | Russell ............................. 604/256 |
| 4,886,501 | 12/1989 | Johnston et al. . |
| 4,929,235 | 5/1990 | Merry et al. ..................... 604/167 |

FOREIGN PATENT DOCUMENTS

| | | |
|---|---|---|
| 0119596 | 3/1984 | European Pat. Off. . |
| 134745 | 8/1984 | European Pat. Off. . |
| 3528878 | 2/1987 | Fed. Rep. of Germany . |

OTHER PUBLICATIONS
Rational Drug Therapy, May, 1988, vol. 22, No. 5, William D. Ensminger M.D. and Ira S. Wollner, M.D.

Primary Examiner—John D. Yasko
Attorney, Agent, or Firm—Harness, Dickey & Pierce

[57] ABSTRACT

An infusion part for implantation adapted for providing repeated access to specific tissue within a patient and communicating with the tissue by an internal implanted catheter. The infusion ports according to this invention incorporate an enlarged entrance orifice with a funnel shaped internal cavity which narrows down to a reduced diameter passageway. An articulating catheter valve is provided within the passageway which normally prevents the flow of fluids through the valve but can be penetrated by an external introduced filament such as a catheter. After implantation, an external filament which is fed through an incision in the patient as is guided by the port internal cavity into registry with the catheter valve. Continued feeding of the filament causes the catheter to pass through the valves. Thereafter, when a catheter is inserted, therapeutic agents infused within the patient, or body fluids can be withdrawn. Alternate embodiments disclose means for providing a change in direction of the an introduced filament inserted through the infusion device. Additional embodiments disclose the concepts of providing a antimicrobial fluid bath within the device for prevention of infection and various approaches for securely connecting an internal catheter to an infusion port.

22 Claims, 6 Drawing Sheets

IMPLANTABLE INFUSION DEVICE

BACKGROUND AND SUMMARY OF THE INVENTION

This invention relates to a device for infusing a therapeutic agent to a desired site within a patient or withdrawing a fluid from a patient, and more particularly, to such a device which is implanted such that no portion is transcutaneous. Its access portion is subcutaneous but designed so as to facilitate repeated access by the percutaneous route.

In current human and animal medical practice, there are numerous instances where therapeutic agents must be delivered to a specific organ or tissue within the body. An example is the infusion of chemotherapy into a central vein on a recurring basis over a lengthy treatment period for widespread sites of malignant tumor. Without an infusion device for intravenous drug infusion, multiple vein punctures over a lengthy period results in progressive thrombosis, venous sclerosis, and destruction of small diameter peripheral vessels. In other cases, it may be desirable to infuse chemotherapy to a localized malignant tumor site. It may be difficult or impossible to deliver an agent specifically to such a site on a regular repetitive basis without surgically implanting an infusion system. Similarly, repeated arterial access is occasionally needed for injection of an X-ray dye or contrast agent into an artery for diagnostic purposes. In certain conditions, there is a need to remove a body fluid repetitively for analysis from a remote body site. Finally, sensing and physiological measuring devices incorporated into small diameter catheters and small diameter optical fibers are increasingly being utilized for monitoring body processes and could be more easily implemented through a properly designed access device with an adequate internal diameter.

In prior medical practice, percutaneous catheters have been used to provide vascular or organ access for drug therapy or removing body fluids. Although such systems generally performed in a satisfactory manner, numerous problems were presented by such therapy approaches, including the substantial care requirements by patients, e.g. dressing changes with sterile techniques, a significant rate of infection of the catheter because of its transcutaneous position, and a high rate of venous thrombosis particularly if the catheter was located within an extremity vein.

Implantable infusion devices or "ports" have recently become available and are a significant advance over transcutaneous catheters. Presently available infusion ports have a number of common fundamental design features. The ports themselves comprise a housing which forms a reservoir which can be constructed from a variety of plastic or metal materials. A surface of the reservoir is enclosed by a high-density, self-sealing septum, typically made of silicone rubber. Connected to the port housing is an outflow catheter which communicates with a vein or other site within the patient where it is desired to infuse therapeutic agents. Implantation of such devices generally proceeds by making a small subcutaneous pocket in the patient under local anesthesia. The internal outflow catheter is tunneled to the desired infusion site. When the physician desires to infuse or remove material through the port, a syringe is used with a hypodermic needle which pierces the skin over the infusion port and through the port septum and into the reservoir.

Although presently available implantable infusion ports generally operate in a satisfactory manner, they have a number of shortcomings. Since these devices rely on a compressed rubber septum for sealing, there are limitations in the diameter of needles which can be used to penetrate the septum, since large diameter needles can seriously damage the septum. These diameter limitations severely restrict the flow rate of fluids passing through the port. In cases where it is desirable to infuse drugs using a flexible external inflow catheter, the catheter must be fed through the needle which penetrates the septum. Such catheters have an extremely small inside diameter and, therefore, impose severe limitations on fluid flow rate.

Presently available implantable drug infusion devices must also have a significant size to provide an acceptable target surface area for the physician who must locate the port and penetrate the septum properly with a needle. The port housing becomes bulky as the septum size increases since structure is required to maintain the septum in compression to provide self-sealing after the needle is removed. Moreover, presently available infusion ports are difficult to clear if thrombosis occurs within them or in the implanted outflow catheter, since it is difficult if not impossible to feed a cleaning wire through the penetrating hypodermic needle in a manner which will clear the infusion device and the internal outflow catheter. Present infusion ports have a retained volume beneath the self sealing septum which increases the volume of drug which must be administered to enable a desired quantity to reach the infusion site. This retained volume also poses problems when a physician desired to deliver drugs to the same infusion site which are incompatible when mixed. In addition when it is desired to withdraw blood through the port, the retained volume of the prior art infusion ports comprises an area where blood clotting can occur, thus interfering with future access to the site. And finally, for present infusion ports, there is a risk that the physician attempting to pierce the port septum will not properly enter it, leading to the possibility of bending or breaking the hypodermic needle.

The present invention relates to various forms of implantable infusion ports which provide numerous enhancements over prior art devices. In accordance with one aspect of the present invention, the infusion port incorporates a funnel shaped entrance orifice which communicates with a reduced diameter exit orifice. An articulating catheter valve is positioned in the infusion port housing between the inlet and outlet orifices which replaces the compressed rubber septum of conventional infusion ports. Various forms of catheter valves can be employed. One such valve is a leaflet valve having one or more flat disks of the elastomeric material having cuts through them to define leaves or flaps which normally resist the flow of fluids across the valve, but can be penetrated by an introduced catheter or other filament.

The infusion ports of this invention are implanted in the same manner as prior art devices. When the physician desires to infuse a therapeutic agent, remove a body fluid, or have vascular access, a slit wound is formed in the skin overlying the infusion port. An external inflow catheter (or other filament) is then fed into the incision with the aid of a guide wire or obturator and into the entrance orifice of the infusion port. The entrance orifice guides the introduced catheter into a proper "docking" position with the articulating catheter valve. By pushing on the externally introduced filament, it is forced through the catheter valve, thereby providing an open communication pathway for the infusion of therapeutic agents, extraction of body fluids, introduction of an optical fiber, clearing by a wire, etc. The introduced filament can be fed into the outflow catheter to any extent desired. In the case of introducing a flexible catheter a guide wire can be inserted into the external catheter to increase its rigidity. Once inserted, the guide wire obturator is removed and material can be infused through the external catheter. The convenient access to the port and internal outflow catheter enables these elements to be cleared with a clearing wire so that they can always be cleared, avoiding the problem of permanent impaction of prior art devices. In addition, the ability to feed a guide wire into the infusion port and internal catheter of this invention enables the internal catheter to be repositioned using a bent or "steerable" guide wire.

The infusion ports having an articulating catheter valve possess the advantage that they have a very small reservoir or "dead space" meaning that virtually all of the infused fluid is throughput to the desired infusion site. This invention, therefore, facilitates infusion of incompatible materials in a serial fashion since there is very little of the previously infused fluid in the device when a subsequent infusion is carried out. This invention also facilitates simultaneous infusion of incompatible materials by using a multi-lumen catheter.

Another aspect of the present invention is a design for an infusion port which is configured such that a line normal to the plane formed by the entrance orifice is nearly at a right angle to the longitudinal axis of the exit passageway. The port access opening guides an introduced filament toward and into the outflow catheter. This approach of guiding a catheter to undergo a bend through the port can be used with conventional port designs having a self-sealing rubber septum. Other aspects of the present invention relate to providing a reservoir within an infusion port for containing an antimicrobial fluid, offering enhanced protection against introduced infection. This invention is further related to various means of securely fastening an outflow catheter to an infusion port.

Additional benefits and advantages of the present invention will become apparent to those skilled in the art to which this invention relates from the subsequent description of the preferred embodiments and the appended claims, taken in conjunction with the accompanying drawings

DETAILED DESCRIPTION OF THE INVENTION

Figure 1:
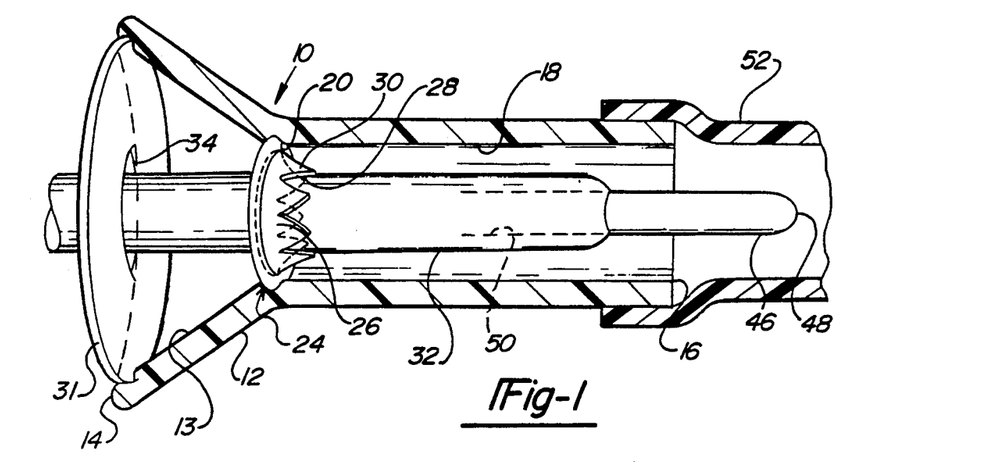
FIG. 1 is a cross-sectional view of an infusion port in accordance with a first embodiment of the present invention shown with an external catheter and obturator inserted through a leaflet type catheter valve.

An infusion port in accordance with a first embodiment of this invention is shown in FIG. 1 and is generally designated there by reference number 10. Infusion port 10 generally comprises housing 12 defining an entrance orifice 14, an inside cavity 13 which funnels down to base 20, with an exit orifice 16, and an elongated passageway 18 extending between the external orifice base, and exit orifice 16. In the embodiment shown, infusion port housing 12 is rotationally symmetrical about a central longitudinal axis passing through passageway 18. As is evident from FIG. 1, the diameter of entrance orifice 14 is preferably several times greater than the internal diameter of passageway 18 (i.e. area difference four times or more). The entire housing 12 can be formed in one piece from numerous polymeric materials or metals which are compatible with human or animal implantation.

Figure 4:
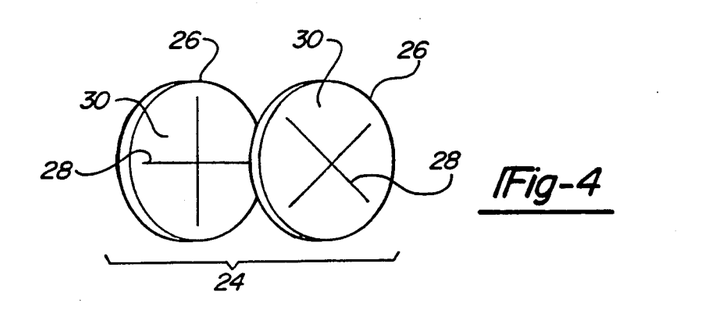
FIG. 4 is a pictorial view of the leaflet valve used with the infusion port of FIG. 1.

Positioned within passageway 18 is leaflet valve assembly 24, which is also shown in an exploded fashion in FIG. 4. Leaflet valve assembly 24 is comprised of one or more thin elastic disks 26 made, for example, from silicone rubber having one or more radial slits 28 cut through them. In the embodiment shown in FIGS. 1 and 4, two disk 26 are provided, each having two slits with a right angle between them so that each defines four leaves 30. The disks 26 are oriented and stacked against one another so that slits 28 of both the disks are angularly misaligned. This misalignment is intentionally provided to enhance the sealing characteristics of valve assembly 24 when it is in its normal closed position, as shown in FIG. 4. Numerous other configurations for valve disk 26 can be provided, such as those incorporating a single slit 28 or any number of additional slits having various numbers of leaves.

The embodiment of infusion port 10 shown in FIG. 1 includes an optional thin rubber septum 31 which acts to shield entrance orifice 14. When a foreign object is implanted in a human, the body often develops fibrous tissue around the object. If an exposed concave pocket is present, such as an open entrance orifice 14, the pocket could possibly become filled with such fibrous tissue. The development of this tissue, should such occur in a patient, might restrict access into the port, and potentially could interfere with the catheter valve function. Therefore, septum 31 provided which is pre-slit at 34 to allow the introduced external filament to easily penetrate the septum. Septum 31 does not, however, provide a fluid-tight barrier as in prior art infusion port which have self-sealing characteristics and is easily penetrated by a blunt instrument. The provision of septum 31 prevents tissue growth inside the housing cavity and also enables the region of housing between entrance orifice 14 and leaflet valve assembly 24 to act as a reservoir for the retention of an antimicrobial fluid which aids in preventing the invasion of infectious agents during use of infusion port 10.

Figure 2:
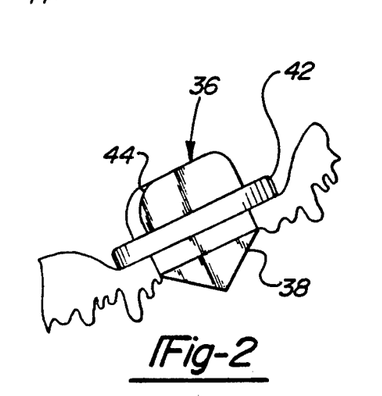
FIG. 2 is a pictorial view of a skin punch which may be used to make an incision into a patient's skin to permit insertion of an external catheter.
Figure 3:
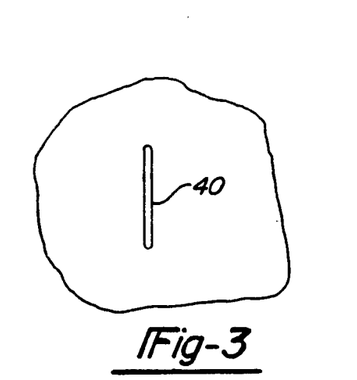
FIG. 3 is an illustration of the stab wound formed by the skin punch shown in FIG. 2.

In use, infusion port 10 is surgically positioned subcutaneously within the patient and mounted to suitable support tissue using conventional mounting techniques, such as sutures or surgical staples. Internal outflow catheter 52 is tunneled to the desired site in the body. When access is desired for the infusion of therapeutic agents, for the sampling of body fluids or for the introduction of physiological sensing elements (electrical or optical or transducers, etc), a flexible external catheter 32 (or other filament) is introduced into infusion port 10, as shown in FIG. 1. Insertion of external catheter 32 can be facilitated using skin punch 36 as shown in FIG. 2. Skin punch 36 includes a pointed flat blade 38 having a width sufficient to make a desired length of an incision 40 shown in FIG. 3. Skin punch 36 includes a radially extending flange 42 which limits the depth of the incision 40. Tab 44 provides convenient means for holding and using skin punch 36. Once external catheter 32 is introduced through stab wound 40, it passes into entrance orifice 14 and is guided by the funnel shaped configuration of the housing cavity into orientation with leaflet valve assembly 24. Continued insertion of external catheter 32 causes the external catheter to penetrate leaflet valve assembly 24, causing deflection of valve leaves 30.

In cases where external catheters 32 are used which are quite flexible, it is necessary to provide localized stiffening of the introduced catheter to facilitate its introduction through the stab wound and into the proper docking position with leaflet valve assembly 24. For such cases, a semi-rigid guide wire or obturator 46 having a blunt end 48 can be used which is inserted through the internal passageway 50 of catheter 32.

Leaflet valve assembly 24 is relatively insensitive to the use of various diameters of external catheter 32, thus providing flexibility for the physician. Furthermore, the characteristics of leaflet valve assembly 24 are such that once external catheter 32 is inserted through the valve, the valve does not exert a large radially inward compressive force on the catheter, thus preventing collapsing of the catheter which would seal off internal passageway 50. However, it does provide sufficient friction on the external catheter to stabilize its position.

Figure 5:
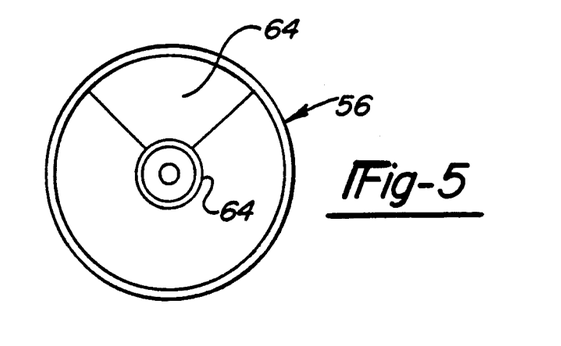
FIG. 5 is a frontal view of a cup type catheter valve which is an alternate embodiment of an articulating catheter valve.
Figure 6:
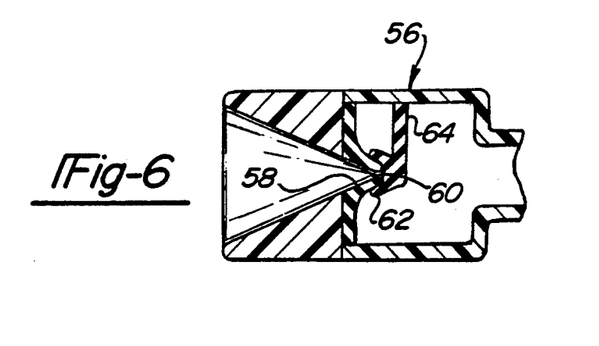
FIG. 6 is a cross-sectional view of the valve of FIG. 5 shown in a closed position.
Figure 7:
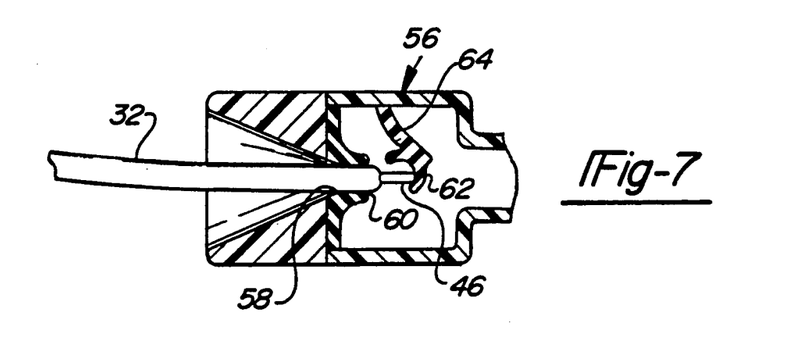
FIG. 7 is a cross-sectional view from FIG. 5 showing the catheter valve in a partly open position.
Figure 8:
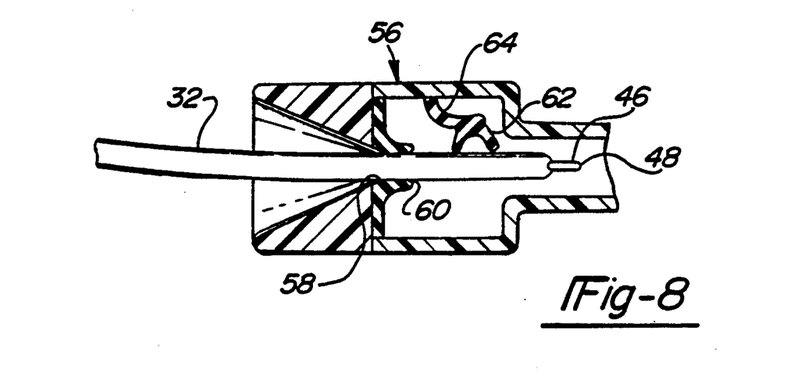
FIG. 8 is a sectional view taken from FIG. 5 showing the catheter valve in a fully open position permitting passage of an introduced catheter.

FIG. 5 illustrates a cup-type catheter valve generally designated by reference number 56. Valve 56 is another articulating type valve which can be used as a replacement for leaflet valve assembly 24 shown in FIG. 1. For this embodiment, a valve passageway 58 is formed which has a generally conically shaped exit nipple 60. A cup shaped closure valve 62 is provided which is supported in cantilever fashion by arm 64 which normally biases the cup closure valve into sealing engagement with exit nipple 60, as shown in FIG. 6. FIG. 7 illustrates catheter valve 56 when external catheter 32, reinforced with obturator 46 is initially penetrating valve passageway 58. During this process, external catheter 32 pushes cup closure valve 62 out of sealing engagement with valve nipple 60. FIG. 8 illustrates a condition of the elements of cup catheter valve 56 once external catheter 32 is fully introduced into the infusion port.

Figure 9:
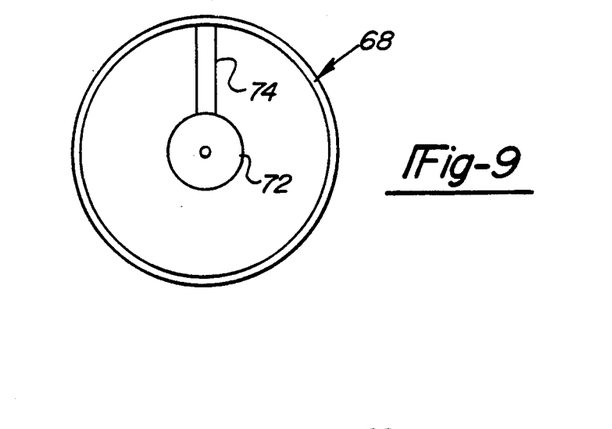
FIG. 9 is a frontal view of a catheter valve of the ball-and-seat variety which is an alternate embodiment of an articulating catheter type valve.
Figure 10:
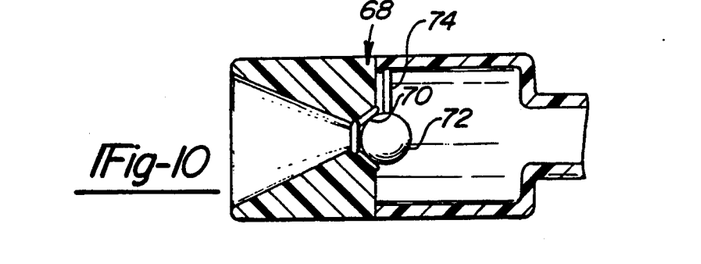
FIG. 10 is a cross-sectional view from FIG. 9 showing the ball catheter valve in a fully closed condition.
Figure 11:
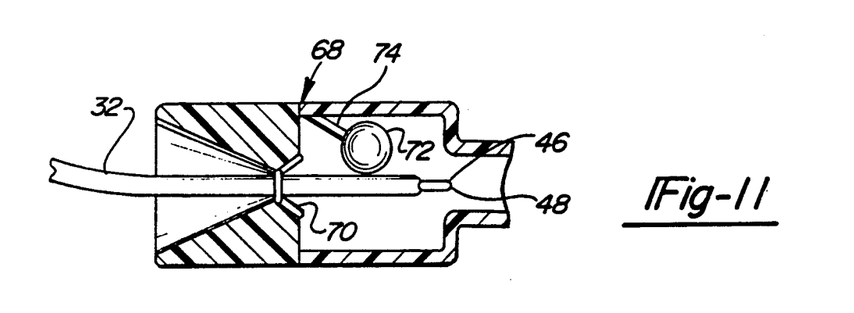
FIG. 11 is a cross-sectional view taken from FIG. 9 showing the ball catheter valve in a fully opened condition.

FIG. 9 illustrates another embodiment for an articulating catheter valve in the form of a ball-and-seat valve, generally designated by reference number 68. Ball-and-seat valve 68 defines a conical ball seat 70 with ball closure valve 72 which is normally biased into sealing engagement with the ball seat by arm 74. Operation of ball-and-seat valve 68 is similar to the operation of cup catheter valve 56 previously described. In both cases, external catheter 32 (or another filament), which may be stiffened by an obturator 46, physically unseats the valve element to permit passage of the external catheter.

Although the leaflet, cup, and ball-in-socket catheter valves described previously differ in their construction, each can be described as an "articulating" valve in that the introduced filament is accurately guided into an insertion area for the valve and has a blunt end which elements of the valves deflect in a predictable and repeatable manner to permit passage of a catheter or other filament. These valve types are distinguishable over prior art septums which are penetrated at random locations and do not define a predictable and defined passageway for a sharp penetrating needle which cuts through and physically damages the septum. Applicants submit that there are numerous additional articulating valve designs which achieve these desired characteristics and are fully applicable to the infusion ports of the present invention.

Figure 12:
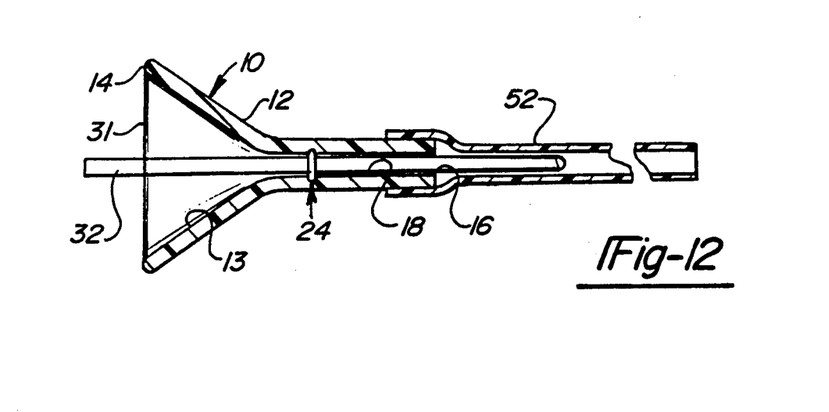
FIG. 12 is a cross-sectional of an embodiment of this invention similar to Figure illustrating that an external introduced catheter may be placed well into the internal outflow catheter of the infusion port.
Figure 13:
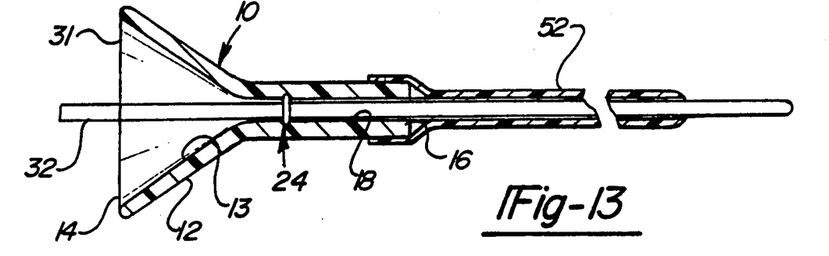
FIG. 13 is a cross-sectional view similar to FIG. 12 except showing the introduced catheter being fed through the infusion port such that its terminal end is beyond the terminal end of the internal outflow catheter.

FIG. 12 illustrates infusion port 10 described previously and shows that once external catheter 32 penetrates leaflet valve assembly 24 (or any other type of articulating valve used), the external catheter can be positioned at any desired point along internal outflow catheter 52. FIG. 13 is a view similar to 12 but shows that external catheter 32 can be fed through infusion port 10 so that its terminal end extends beyond that of internal catheter 52. This feature allows infusion port 10 to be readily adapted for angiography and angioplasty procedures.

Figure 14:
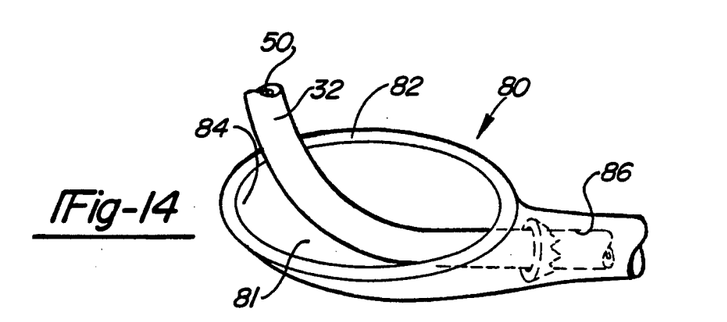
FIG. 14 is a pictorial view of an infusion port in accordance with a second embodiment of this invention shown providing a change in angle for the external introduced catheter.
Figure 15:
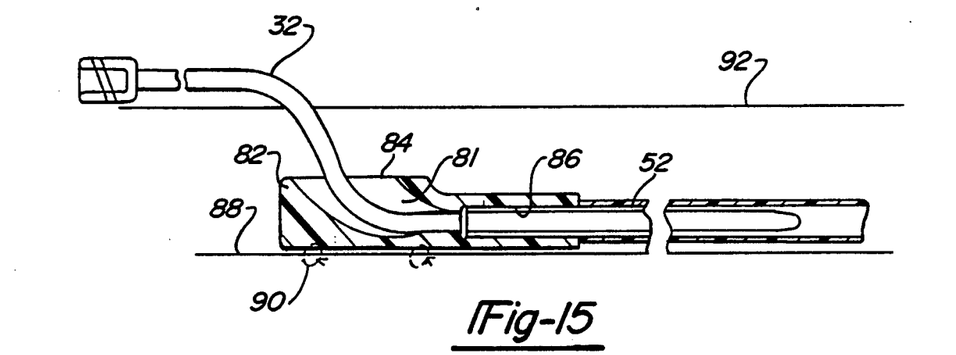
FIG. 15 is a cross-sectional view taken to the infusion port of FIG. 14 showing the infusion port in use and showing an external introduced catheter in position for infusion of the patient.

Now with reference to FIGS. 14 and 15, a second embodiment of an infusion port according to this invention is shown which is generally designated by reference number 80. Infusion port 80 differs principally from infusion port 10 in that the internal cavity 81 of housing 82 is in the shape of a bent or twisted funnel or horn such that a line normal to the plane defined by entrance orifice 84 is generally at a right angle to the longitudinal central axis of exit passageway 86. Like the first embodiment, infusion port 80 employs an articulating catheter valve, such as a leaflet valve assembly 24 as previously described.

Infusion port cavity 81 has a smooth inside surface which is shaped to have a decreasing cross section area from entrance orifice 84 to exit passageway 86 for guiding external catheter 32 into registry with the exit passageway. The configuration of infusion port 80 is desirable where a large target area is needed which is generally parallel to the surface of the patients skin overlying the device. In all other respects, infusion port 60 is constructed and used in the manner consistent with that of infusion port 10 previously described. FIG. 15 provides an illustration of infusion port 80 in use for infusing a patient. Port 80 is shown fastened to support tissue 88 by sutures 90 below skin 92 of the patient.

Figure 16:
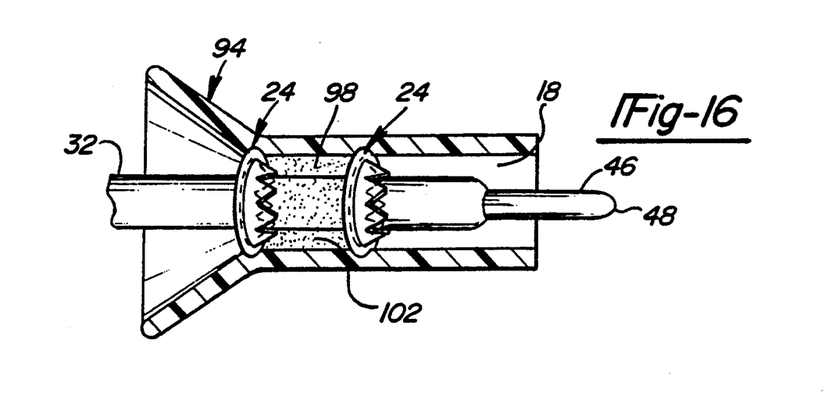
FIG. 16 is a partial cross-sectional view of a infusion port in accordance with a third embodiment of this invention shown employing a pair of separated leaflet valves which provide a reservoir for an antimicrobial fluid which provides enhanced resistance against infection.

FIG. 16 is a partial sectional view of an infusion port 94 according to a third embodiment of this invention. This embodiment differs from those described previously in that a pair of leaflet valve assemblies 24 is provided along internal passageway 18 to define an enclosed internal cavity 98. Internal cavity 98 is provided so that an antimicrobial solution 102 can be retained as a means of inhibiting &.he introduction of infectious agents into the patient through the process of infusion.

Figure 17:
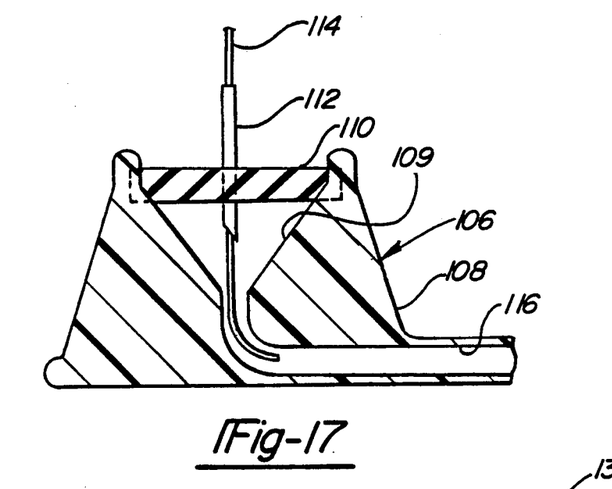
FIG. 17 is a cross-sectional view of an infusion port in accordance with a third embodiment of this invention employing a conventional rubber septum but having means for guiding a catheter or guide wire through a bend and into or beyond the port exit orifice.

FIG. 17 illustrates an infusion port in accordance with a fourth embodiment of this invention which is designated by reference number 106. Like the second embodiment shown in FIG. 14, infusion port housing 108 has an internal cavity 109 which causes an external catheter or other filament to undergo a right angle bend as it is fed into the device. However, infusion port 106 does not incorporate an articulating catheter valve, but rather uses the conventional approach of using a compressed rubber septum 110. In use of this embodiment, a hypodermic needle 112 penetrates septum 110 and a small diameter catheter 114 is fed through needle 112.

As discussed previously in connection with FIG. 14, the internal surface configuration of housing cavity 109 causes catheter 114 to be guided into and through passageway 116, and if desired, into the attached internal catheter (not shown). This embodiment also provides the advantages that a guide wire can be fed through needle 112 to clear thrombosis or other obstructions occurring within the device or in the attached internal catheter.

Figure 18:
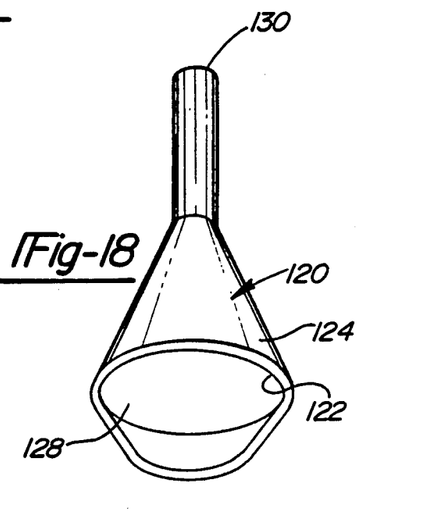
FIG. 18 is an infusion port in accordance with a fourth embodiment of this invention having an elliptically shaped entrance mouth.
Figure 19:
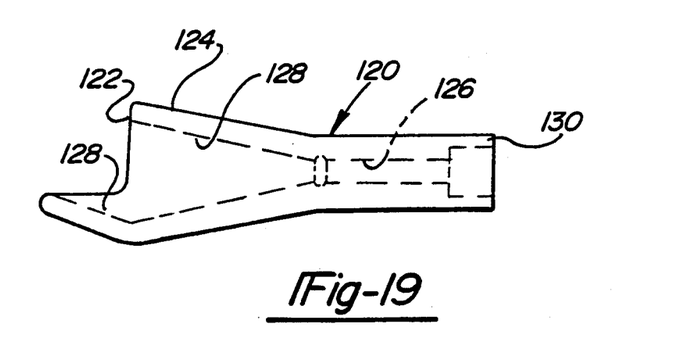
FIG. 19 is a side view of the infusion port shown in FIG. 18.

FIGS. 18 and 19 illustrate an embodiment of infusion port 120 according to a fifth embodiment of the invention which may have an articulating catheter valve as described previously, or may employ a compressed rubber septum like that of the embodiment shown in FIG. 17. These figures, however, illustrate that entrance opening 122 can form a generally elliptical configuration such that the target area for the infusion port has is greatest area when entering the device from a direction between alignment with the exit passageway 126, or at right angle to exit passageway. In other words, a line normal to entrance opening 122 forms an obtuse angle to the axis of exit passageway 126. Like the prior embodiments, housing 124 has a smooth internal surface which is shaped to guide an introduced cavity 128 with external catheter into exit passageway 126.

Figure 20:
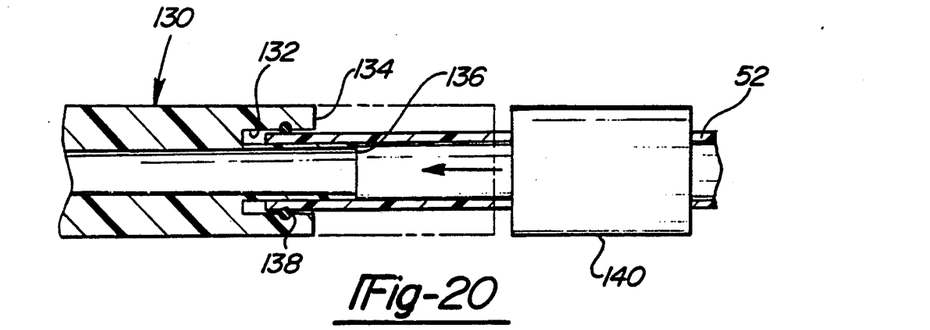
FIG. 20 is a cross-sectional view illustrating a manner of connecting an internal outflow catheter to an infusion port in accordance with this invention, incorporating an annular chamber for receiving the outflow catheter.

FIGS. 20 through 23 illustrate various means for attaching an internal outflow catheter 52 to an infusion port. For the embodiment of FIG. 20, the infusion port features an exit end 130 defining an annular gap 132 formed between an outer tubular portion 134 of the exit outlet 134 and an inner tubular portion 136. Outflow catheter 52 is slid onto inner tube 136 and into annular gap 132. Sealing means such as a gasket or O-ring 138 can be provided to enhance the integrating of the fluid tight connection. Compression ring 140 can be used which is slid onto the connection as shown in FIG. 20 to exert a compressive force on outflow catheter 52, further securing it to the infusion port. Compression ring 140 also acts as a stress reliever to prevent kinking of the outflow catheter 52 at its connection point to the infusion port.

Figure 21:
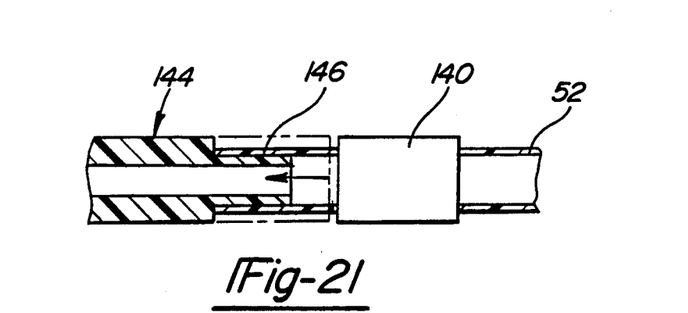
FIG. 21 is a cross-sectional view of another means of attaching an internal outflow catheter to an infusion port according to this invention, in which the catheter is placed over a smooth cylindrical surface and a compression ring is slid onto the junction.

FIG. 21 illustrates another means for connecting outflow catheter 52 to an infusion port. In this embodiment, exit end 144 has a reduced diameter projecting nipple 146 which outflow catheter 152 is slid over. Like the embodiment shown in FIG. 20, compression ring 140 is provided which is slid onto the connection to provide the benefits mentioned previously in connection with FIG. 20.

Figure 22:
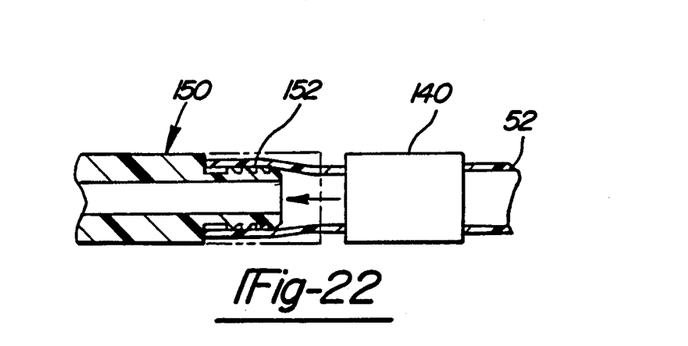
FIG. 22 is a cross-sectional view of still another approach toward connecting an internal outflow catheter to an infusion port incorporating a barbed nipple on the infusion port and a compression ring.

FIG. 22 illustrates an infusion port exit end 150 which features reversely oriented barbs 152 which serve to securely engage the inner surface of outflow catheter 52. Again, compression ring 140 is used to enhance the security of the connection of the outflow catheter to exit end 150.

Figure 23:
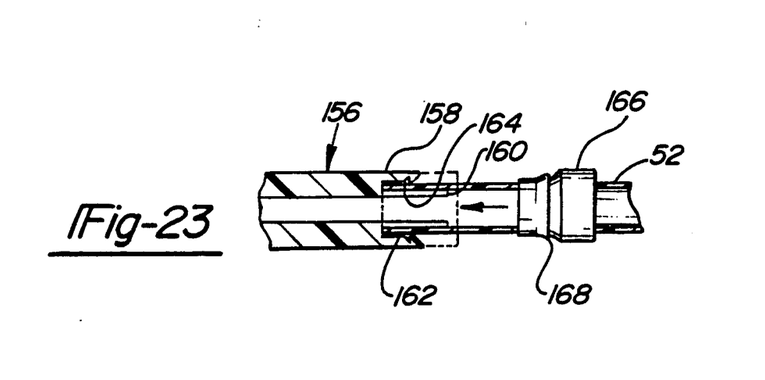
FIG. 23 is another means of attaching an internal outflow catheter to an infusion port according to this invention incorporating an interlocking compression ring.

FIG. 23 illustrates still another approach toward connecting outflow catheter 52 to an infusion port exit end 156. This embodiment, like that shown in FIG. 20, defines an outer tubular portion 158, an inner tubular portion 160, with annular gap 162 therebetween. For this embodiment, however, the inside diameter surface of outer tubular portion 158 defines groove 164. Compression ring 166 has an exterior configuration including annular barb 168 which interlocks with groove 164 when the compression ring is slid onto exit end 156.

While the above description constitutes the preferred embodiments of the present invention, it will be appreciated that the invention is susceptible of modification, variation and change without departing from the proper scope and fair meaning of the accompanying claims.

We claim:

1. An implantable patient access device for permitting access to an internal catheter by a flexible filament such as an external catheter, wire or optical fiber comprising:

a housing defining an entrance orifice and a single exit orifice with said entrance orifice having a cross-sectional open area which decreases from said entrance orifice to a passageway communicating with said exit orifice, said housing causing said filament introduced into said entrance orifice to be directed to enter and pass through said passageway, at least one articulating catheter valve positioned with said housing passageway which normally remains closed to provide resistance to flow of fluids through said valve, yet opens when contacted to permit said filament to pass through said valve enabling said filament to communicate with said internal catheter through said exit orifice, and mounting means formed by said housing for enabling a fastener to affix said housing subcutaneously.

2. An implantable patient access device according to claim 1 wherein said catheter valve comprises a leaflet valve having a generally circular flat disk of a resilient material with at least one cut through said disk which crosses the center of said disk.

3. An implantable patient access device according to claim 2 wherein said device includes at least two of said leaflet valves which are stacked together and are oriented so that said cuts of a first of said valves are not aligned with said cuts of a second of said valve disks.

4. An implantable patient access device according to claim 1 wherein said catheter valve comprises a cup valve having a nipple with an exit side and a valve cup for sealing engagement with said nipple, and means for resiliently urging said cup to seal against said nipple, and said cup valve oriented such that said filament unseats said cup from said nipple when introduced into said access device.

5. An implantable patient access device according to claim 1 wherein said catheter valve comprises a ball-and-seat type valve wherein said ball sealingly engages with a seat formed by said access device and said ball is urged to unseat from said seat when said filament is introduced into said access device.

6. An implantable patient access device according to claim 1 wherein said access device comprises at least two of said articulating catheter valves positioned within said housing and separated to define an antimicrobial fluid reservoir.

7. An implantable patient access device according to claim 1 wherein said device further comprises an elastic septum covering said entrance orifice and having a preformed slit therethrough.

8. An implantable patient access device according to claim 1 wherein said entrance orifice defines a generally circular perimeter and wherein said passageway is an elongated cylindrical bore with said entrance orifice concentric with said passageway.

9. An implantable patient access device according to claim 1 wherein said entrance orifice defines a generally circular perimeter lying on a plane positioned such that a line normal to said plane forms a right angle to the central axis of said passageway with said housing orifice shaped to guide said filament inserted into said entrance orifice to bend and become inserted through said catheter valve.

10. An implantable patient infusion access according to claim 1 wherein said entrance orifice defines a plane which is oriented such that a line normal to said plane forms an obtuse angle with respect to a central longitudinal axis through said exit orifice.

11. An implantable patient access device according to claim 1 wherein said entrance orifice has a cross-sectional area at least four times that of the cross-sectional area of said passageway.

12. An implantable patient access device according to claim 1 wherein said access device exit orifice defines an annular pocket formed between inner and outer tubular portions with an end of said internal catheter fitting over said inner tubular portion and within said annular pocket.

13. An implantable patient access device according to claim 1 further comprising a compression ring for compressing said internal catheter radially inwardly against said access device housing.

14. An implantable patient access device according to claim 1 further comprising a compression ring for comprising an end of said internal catheter attached to said access device radially inwardly against said access device housing.

15. An implantable patient access device according to claim 1 wherein said access device exit orifice defines an externally ribbed nipple with an end of said internal catheter positioned around said nipple.

16. An implantable patient access device according to claim 15 further comprising a compression ring for compressing said internal catheter end radially inwardly against said access device housing.

17. An implantable patient access device according to claim 1 wherein said access device exit orifice defines an annular gap formed between an inner and outer tubular portion, with an end of the internal catheter disposed within said gap and having a compression ring having means for interlocking with said outer tubular portion.

18. A method for permitting repeated access to preselected tissue within a patient by a filament such as an external catheter, wire or optical fiber, comprising the steps of:

providing an implantable access device having an enlarged funnel shaped entrance orifice and a single exit orifice with an articulating catheter valve positioned between said orifices which normally resists the flow of fluids through said valve, providing an internal catheter connectable to said device exit orifice, making an incision in the patient's skin, implanting said device subcutaneously within the patient, mounting said access device to subcutaneously patient tissue using a fastener engaging a mounting feature of said device, positioning said internal catheter to communicate from the device exit orifice to said preselected tissue, providing a flexible filament, inserting said filament through an incision and into said device entrance orifice, and feeding said filament through said articulating catheter valve, thereby providing said access to said preselected tissue.

19. The method according to claim 18 further comprising the steps of:

providing a skin punch having a flat elongated blade with a flange and making said incision by pushing said punch against the patient's skin causing said blade to cut the skin and said flange limiting the depth of said incision.

20. The method according to claim 18 further comprising the step of providing a semi-rigid guide wire and inserting said wire into an external catheter to add rigidity to said external catheter to facilitate insertion of said catheter.

21. A method for permitting repeated access to preselected tissue within a patient by a filament such as an external catheter, wire or optical fiber, comprising the steps of:

providing an implantable access device having an enlarged funnel shaped entrance orifice, and an exit orifice with an articulating catheter valve positioned between said orifices which normally resists the flow of fluids through said valve, providing an internal catheter connectable to said device exit orifice, providing a skin punch having a flat elongated blade with a flange, making an incision in the patient's skin by pushing said punch against the patient's skin causing said blade to cut the skin and said flange limiting the depth of said incision, implanting said device subcutaneously within a patient, positioning said internal catheter to communicate from the device exit orifice to said preselected tissue, providing a flexible filament, inserting said filament through an incision and into said device entrance orifice, and feeding said filament through said articulating catheter valve, thereby providing said access to said preselected tissue.

22. A method for permitting repeated access to preselected tissue within a patient by an external catheter, comprising the steps of:

providing an implantable access device having an enlarged funnel shaped entrance orifice, and an exit orifice with an articulating catheter valve positioned between said orifices which normally resists the flow of fluids through said valve, providing an internal catheter connectable to said device exit orifice, making an incision in the patient's skin, implanting said device subcutaneously within the patient, positioning said internal catheter to communicate from the device to said preselected tissue, providing a semi-rigid guide wire and inserting said wire into said external catheter to add rigidity to said external catheter to facilitate insertion of said external catheter, inserting said external catheter through said incision and into said device entrance orifice, and feeding said external catheter through said articulating catheter valve, thereby providing said access to said preselected tissue.

* * * * *

UNITED STATES PATENT AND TRADEMARK OFFICE
CERTIFICATE OF CORRECTION

PATENT NO. : 5,057,084

DATED : October 15, 1991

INVENTOR(S) : William D. Ensminger et al

It is certified that error appears in the above-identified patent and that said Letters Patent is hereby corrected as shown below:

In the Abstract, Line 1, "part" should read --port--.

In the Abstract, Line 15, "valves" should read --valve--.

Column 7, Line 55, delete "&.he" and insert in place thereof --the--.

Column 9, Line 15, Claim 1, "with" should read --within--.

Column 10, Line 53, Claim 18, "subcutaneously" should read --subcutaneous--.

Signed and Sealed this

Thirty-first Day of August, 1993

*Attest:*

BRUCE LEHMAN

*Attesting Officer*     *Commissioner of Patents and Trademarks*